United States Patent [19]
Kishida et al.

[11] Patent Number: 5,844,658
[45] Date of Patent: Dec. 1, 1998

[54] EYE FUNDUS TRACKING APPARATUS AND EYE FUNDUS BLOOD FLOW METER USING THE SAME

[75] Inventors: Nobuyoshi Kishida; Toshikazu Tamura, both of Utsunomiya, Japan

[73] Assignee: Canon Kabushiki Kaisha

[21] Appl. No.: 754,652

[22] Filed: Nov. 21, 1996

[30] Foreign Application Priority Data

Nov. 22, 1995 [JP] Japan .................................. 7-328019

[51] Int. Cl.⁶ ........................................................ A61B 3/14
[52] U.S. Cl. .......................................... 351/206; 351/209
[58] Field of Search ................................. 351/200, 205, 351/206, 209, 210, 221; 396/18

[56] References Cited

U.S. PATENT DOCUMENTS

| | | | |
|---|---|---|---|
| 5,098,426 | 3/1992 | Sklar et al. | 351/209 X |
| 5,640,963 | 6/1997 | Tanaka | 128/665 |

FOREIGN PATENT DOCUMENTS 1-028133  1/1989  Japan .

*Primary Examiner*—Huy Mai
*Attorney, Agent, or Firm*—Fitzpatrick, Cella, Harper & Scinto

[57] ABSTRACT

This specification discloses an eye fundus blood flow meter having a blood flow measuring system for measuring the blood flow of the fundus of an eye to be examined, and a malfunction detecting unit for detecting measurement malfunction occurring during the measurement by the blood flow measuring system. The specification also discloses an eye fundus tracking apparatus for tracking a predetermined position on the fundus of an eye to be examined having a tracking mechanism for tracking a predetermined position on the eye to be examined, an abnormality detecting system for detecting the operational abnormality of the tracking mechanism, and a control unit for executing predetermined control on the tracking mechanism when the operational abnormality occurs.

7 Claims, 13 Drawing Sheets

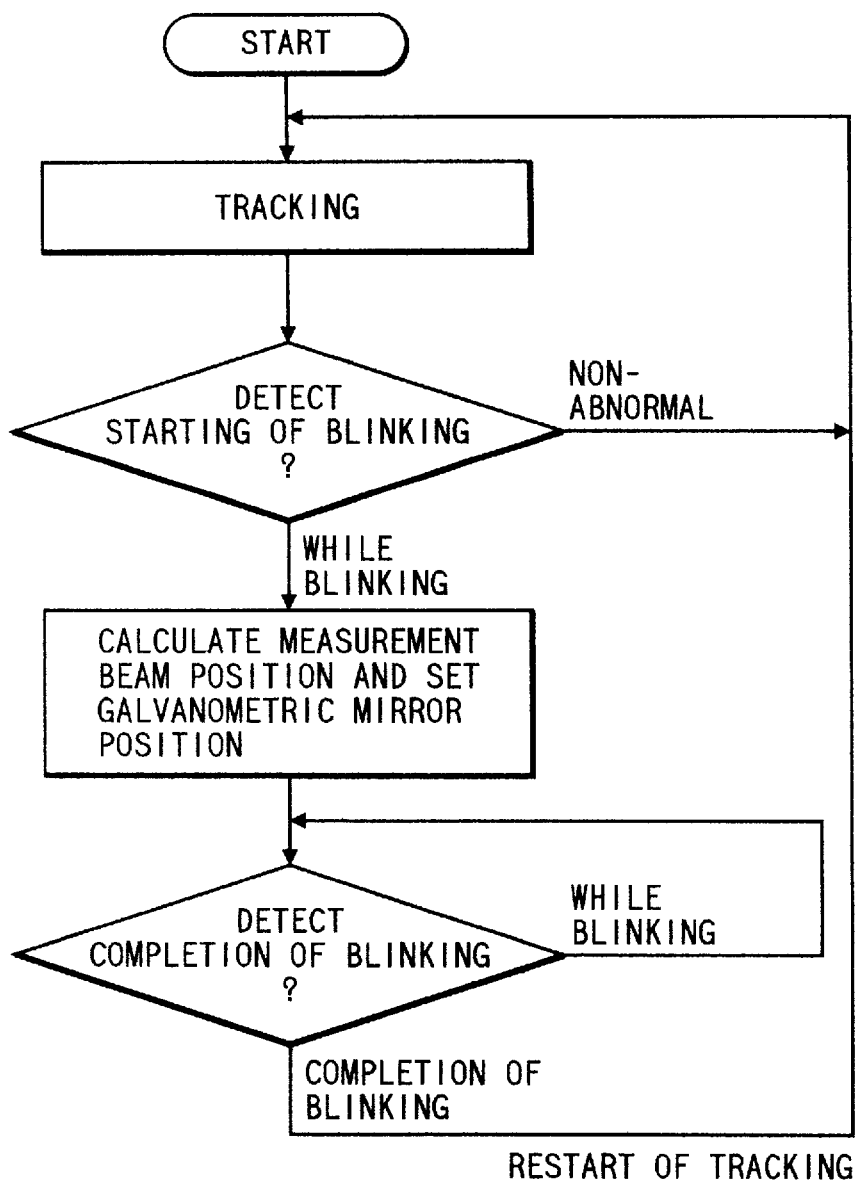

EYE FUNDUS TRACKING APPARATUS AND EYE FUNDUS BLOOD FLOW METER USING THE SAME

BACKGROUND OF THE INVENTION

1. Field of the Invention

This invention relates to an eye fundus blood flow meter for measuring the condition of a blood flow in a blood vessel of the fundus of an eye and an eye fundus tracking apparatus.

2. Related Background Art

FIG. 1A of the accompanying drawings shows an example of an eye fundus blood flow meter according to the conventional art, in which a slit lamp usually used for ophthalmologic diagnosis has been adapted for blood flow measurement. An illuminating optical system is disposed on an optical path K1, and a white light beam from a light source 1 for observation is reflected by an apertured mirror 2 and illuminates a blood vessel Ev on the fundus Ea of an eye E to be examined through a slit 3, a lens 4 and a contact lens 5 for offsetting the refractive power of the cornea of the eye E to be examined and making the fundus Ea of the eye observable. Also, a light source 6 for measurement, emitting an He-Ne laser beam for measurement, is disposed on an optical path behind the apertured mirror 2, and the measurement light from the light source 6 for measurement passes through the central opening portion of the apertured mirror 2 and is made coaxial with the light beam from the light source 1 for observation and irradiates the fundus Ea of the eye in a spot-like form.

Light scattered and reflected by blood corpuscles flowing through the blood vessel Ev and the blood vessel wall passes through the objective lenses 7a and 7b of light receiving optical systems for stereoscopic observation, disposed on optical paths K2 and K3 forming an angle $\alpha'$ therebetween, is reflected by mirrors 8a, 8b and mirrors 9a, 9b and is observed as the image of the fundus of the eye by an examiner through eyepieces 10a and 10b, and the examiner looks into the eyepieces 10a and 10b and selects a region to be measured while observing the fundus Ea of the eye.

FIG. 1B of the accompanying drawings shows the image of the fundus of the eye observed by the examiner, and when the blood vessel Ev to be measured in an area being illuminated by the illuminating light is made coaxial with a scale Sc prepared in advance on the focal planes of the eyepieces 10a and 10b, the laser beam from the light source 6 for measurement and the blood vessel Ev are made coaxial with each other, and the region to be measured is determined by the spot light beam Ps from the light source 6 for measurement. At this time, the reflected light beam on the fundus Ea of the eye by the measurement light is received by photomultipliers 12a and 12b through optical fibers 11a and 11b.

This light reception signal includes a predetermined beat signal component created by a component Doppler-shifted by blood flowing through the blood vessel Ev and a component reflected by the blood vessel wall, which is stationary, interfering with each other, and this beat signal can be frequency-analyzed to thereby find the velocity of the blood flow in the blood vessel Ev.

FIG. 1C of the accompanying drawings shows an example of the result of frequency analysis of the light reception signal measured by the photomultipliers 12a and 12b, and axis of the abscissas represents the frequency $\Delta f$ and the axis of the ordinates represents the output $\Delta S$ thereof. The relation among the maximum value $\Delta$fmax of the frequency, the wave number vector $\kappa i$ of the incident light beam, the wave number vector $\kappa s$ of the received light beam and the velocity vector $v$ of the blood flow can be expressed as $$\Delta \text{fmax} = (\kappa s - \kappa i) \cdot v \tag{1}$$

Accordingly, when expression (1) is modified by the use of the maximum values $\Delta$fmax1 and $\Delta$fmax2 of the frequency calculated from the respective light reception signals of the photomultipliers 12a and 12b, the wavelength $\lambda$ of the laser beam, the refractive index n of the region to be measured, the angle $\alpha$ formed between light receiving optical axes K2 and K3 in the eye, and the angle $\beta$ formed between the plane made by the light receiving optical axes K2 and K3 in the eye and the velocity vector v of the blood flow, the maximum blood flow velocity Vmax can be expressed as $$V\text{max} = \{\lambda/(n \cdot \alpha)\} \cdot |\Delta \text{fmax1} - \Delta \text{fmax2}|/\cos\beta. \tag{2}$$

By measurement being thus effected from two directions, the contribution of the measurement light in the direction of incidence thereof is offset, and the blood flow in any region on the fundus Ea of the eye can be measured.

Further, assuming that the blood vessel Ev is cylindrical, the blood flow quantity Q is expressed as $$Q = (\pi \alpha^2/4) \cdot (V\text{max}/2), \tag{3}$$

where $\alpha$ is the diameter of the blood vessel Ev.

Also, to measure the true velocity of the blood flow from the line of intersection A between the plane formed by the two light receiving optical paths K2, K3 shown in FIG. 1A and the fundus Ea of the eye, and the angle $\beta$ formed between the velocity vector v of the blood flow and the line of intersection A, it is necessary to make the line of intersection A coincident with the velocity vector v, with $\beta = 0°$ being assumed in expression (2). Therefore, in the example of the prior art, the entire light receiving optical system is rotated or an image rotator is disposed in the light receiving optical system so that the line of intersection A may be made optically coincident with the velocity vector.

In this apparatus, however, the slit lamp is the base and therefore, the eye E to be examined must wear a contact lens when the observation of the fundus of the eye is effected. Thus, the contact lens affects the state of the blood flow on the fundus of the eye.

In order to eliminate such an ill effect of the contact lens, an apparatus using a unique optical system is disclosed in Japanese Laid-Open Patent Application No. 1-28133. In this apparatus, however, the fact that the eye E to be examined can move freely makes it difficult to project a measurement beam always onto a blood vessel which is the object of measurement. Accordingly, two galvanometric mirrors, of which the axes of rotation are orthogonal to each other, are disposed at a position conjugate with the center of turning of the eye E to be examined, and an eye fundus tracking apparatus for controlling these galvanometric mirrors by the output from photographing means is added to thereby project a tracking beam onto the blood vessel in the fundus of the eye so that the blood vessel image by the beam may be picked up and the optical system may be controlled by the use of a signal indicative of the position of the image to thereby always hold a measurement beam on the blood vessel to be measured.

However, when use is made of the eye fundus tracking apparatus and the eye fundus blood flow meter as described above, there arises the necessity of considering also the situation when an abnormal state such as an examinee's blink has occurred.

SUMMARY OF THE INVENTION

In view of the above-described example of the conventional art, the present invention has as an object thereof to provide an eye fundus tracking apparatus which, even when an abnormal state such as a blink occurs, can resume tracking after the termination of the abnormal state and/or an eye fundus blood flow meter which avoids becoming incapable of measuring the blood flow after the occurrence of the abnormal state and can resume measurement after the termination of the abnormal state.

Other objects of the present invention will become apparent from the following description of some embodiments of the invention.

BRIEF DESCRIPTION OF THE DRAWINGS

FIG. 14 is a flow chart of the operation of resuming automatic tracking by the detection of a blink.

DESCRIPTION OF THE PREFERRED EMBODIMENTS

The invention will hereinafter be described in detail with respect to some embodiments thereof shown in FIGS. 2A and 2B to 14.

Figure 2A:
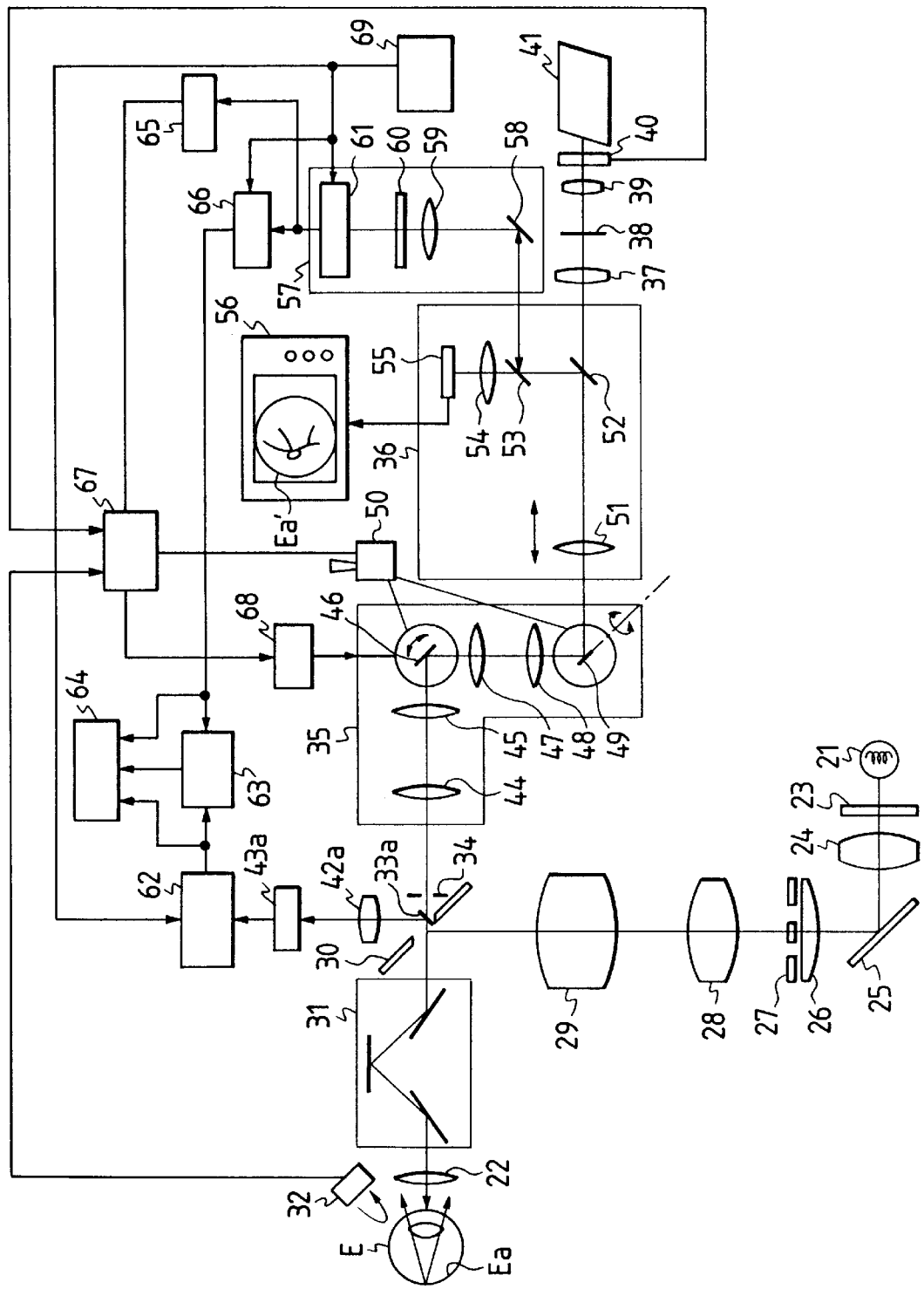
FIG. 2A shows the construction of a first embodiment of the present invention.

Referring to FIG. 2A, which shows the construction of an eye fundus camera according to a first embodiment, on an optical path leading from an illuminating light source 21, such as a tungsten lamp emitting visible light, to an objective lens 22, there are disposed in succession a band-pass filter 23 transmitting yellow-green light therethrough, a condenser lens 24, a mirror 25, a field lens 26 for making an eye E to be examined efficiently receive a light beam, a ring slit 27 having a ring-shaped opening portion, relay lenses 28, 29, an apertured mirror 30 and an image rotator 31. A blink detecting unit 32 is provided near the objective lens 22.

On an optical path behind the apertured mirror 30, there are disposed in succession a pair of small mirrors 33a and 33b, an aperture 34, an image stabilizer 35, an observation optical system 36, a lens 37, an aperture 38, a lens 34, an ND filter changeover portion 40 and a light source 41 for measurement emitting an He-Ne laser beam. On the optical paths in the directions of reflection of the pair of small mirrors 33a and 33b, there are disposed lenses 42a, 42b and photomultipliers 43a, 43b. In FIG. 2A, only the member on the optical axis of the small mirror 33a is shown to avoid overlapping.

In the image stabilizer 35, there are arranged in succession lenses 44, 45, a galvanometric mirror 46, lenses 47, 48 and a galvanometric mirror 49, and the galvanometric mirrors 46 and 49 are adapted to be rotated by the operation of an operating rod 50 attached to the outside. In this image stabilizer 35, the fundus Ea of the eye is made conjugate with the galvanometric mirror 46 by the lenses 44, 45, and conjugate with the galvanometric mirror 49 by the lenses 47, 48.

In the observation optical system 36, there are provided a focusing lens 51 movable on the optical path and a dichroic mirror 52, and in the direction of reflection of the dichroic mirror 52, there are arranged a half mirror 53, a lens 54 and a television camera 55, the output of which is connected to a monochromatic television monitor 56. Also, in the direction of reflection of the half mirror 53, there is provided a blood vessel detecting system 57 and there are arranged a mirror 58, a lens 59, a filter 60 and a one-dimensional CCD sensor 61 with an image intensifier.

The outputs of the photomultipliers 43a and 43b are connected to the input side of a blood flow velocity calculating unit 62, the output of which is connected to a blood flow quantity calculating unit 63 and a display unit 64, and the output of the blood flow quantity calculating unit 63 is connected to the display unit 64. The output of the CCD sensor 61 is connected to tracking control means 65 and a blood vessel diameter calculating unit 66, the output of the tracking control means 65 is connected to a drive circuit 68 for driving the galvanometric mirrors 46 and 49 through a control device 67, and the output of the blood vessel diameter calculating unit 66 is connected to the blood flow quantity calculating unit 63 and the display unit 64. Also, the outputs of the blink detecting portion 32 and the operating rod 50 are connected to the control device 67, and the output signal SS of a synchronizing signal generating circuit 69 is connected to the CCD sensor 61, the blood flow velocity calculating unit 62 and the blood vessel diameter calculating unit 66.

Figure 2B:
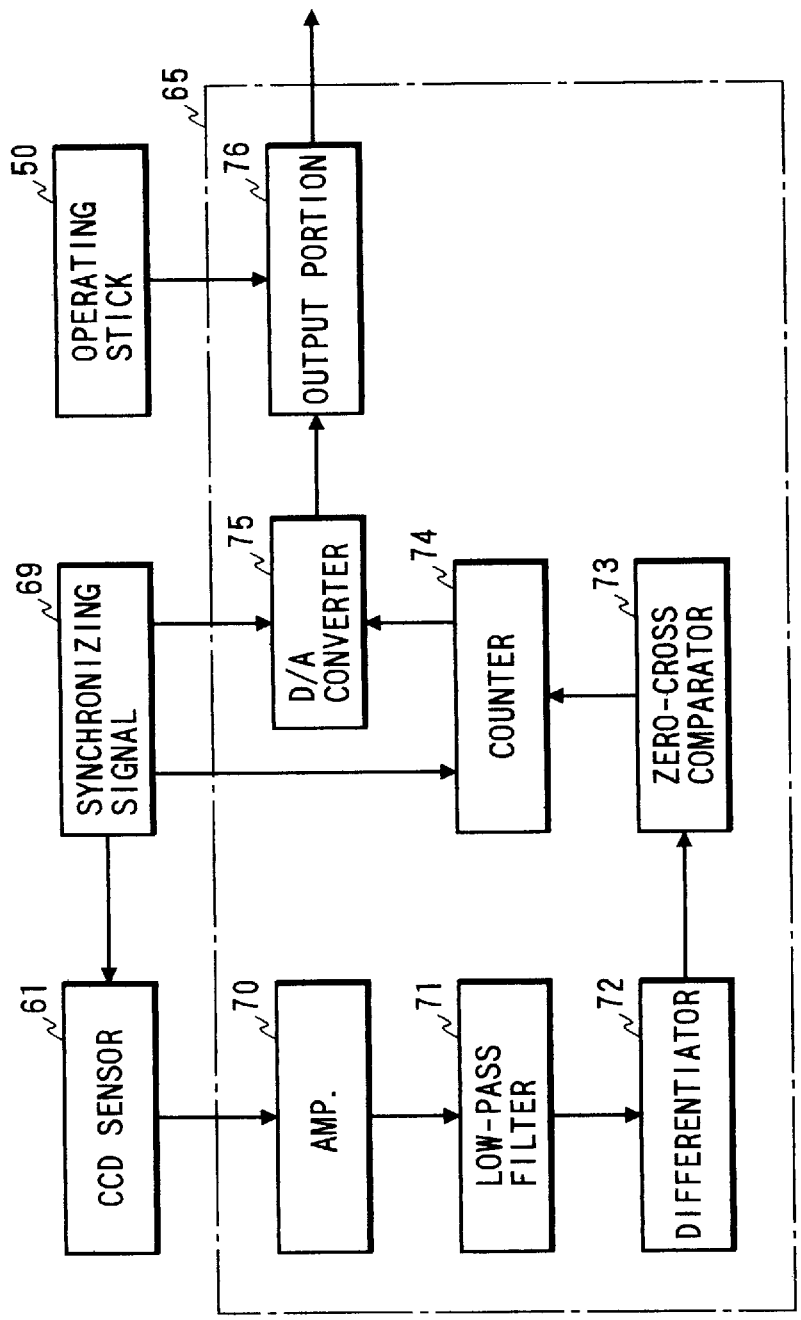
FIG. 2B is a block circuit diagram of tracking control means.

FIG. 2B shows a block circuit diagram of the tracking control means 65, and the output of the CCD sensor 61 is connected to a differentiator 72 via an amplifier 70 and a low-pass filter 71. The output of the differentiator 72 is connected to a counter 74 through a zero-cross comparator 73, and the output of the counter 74 is connected from an output portion 76 to the control device 67 through a D/A converter 75. Also, the design of the device is such that the synchronizing signal SS of the synchronizing signal generating circuit 69 is inputted to the CCD sensor 61, the counter 74 and the D/A converter 75.

Figure 3:
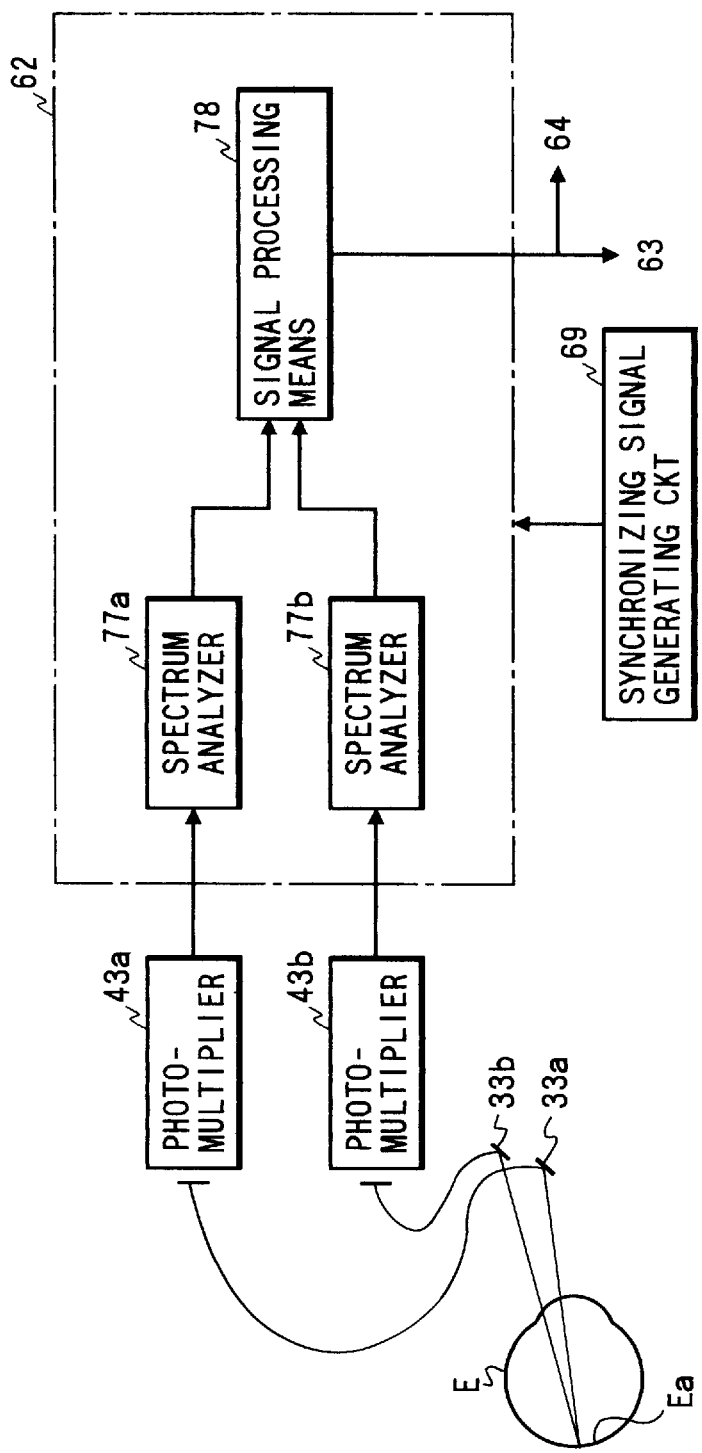
FIG. 3 is a block circuit diagram of a blood flow velocity calculating unit.

Referring to FIG. 3, which shows a block circuit diagram of the blood flow velocity calculating unit 62, the blood flow velocity calculating unit 62 is comprised of two spectrum analyzers 77a, 77b and signal processing means 78 for receiving the signals thereof. The outputs of the photomultipliers 43a and 43b, receiving the reflected lights from the pair of small mirrors 33a and 33b, are connected to the spectrum analyzers 77a and 77b, and the output of the signal processing means 78 is connected to the blood flow quantity calculating unit 63 and the display unit 64.

Figure 4:
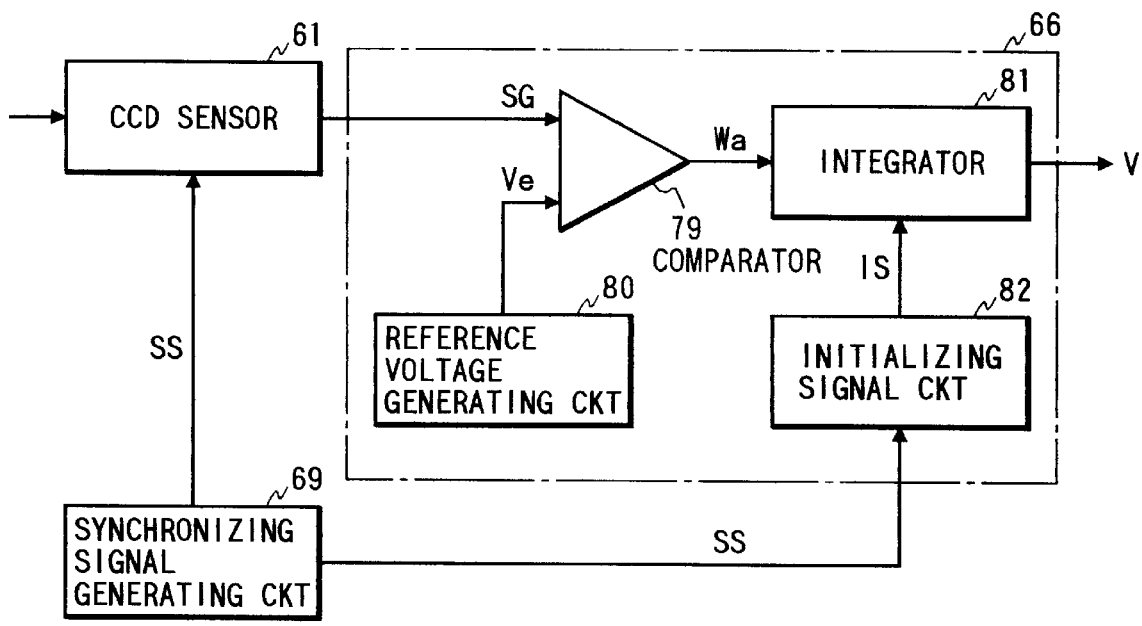
FIG. 4 is a block circuit diagram of a blood vessel diameter calculating unit.

Referring to FIG. 4, which shows a block circuit diagram of the blood vessel diameter calculating unit 66, the output SG of the CCD sensor 61 and the reference voltage output Ve of a reference voltage generating circuit 80 are connected to the comparator 79 of the blood vessel diameter calculating unit 66, and the output Wa of the comparator 79 is connected to an integrator 81 so that a blood vessel diameter signal may be outputted to the integrator 81. Also, the output IS of an initializing signal circuit 82 is connected to the integrator 81, and the synchronizing signal SS of the synchronizing signal generating circuit 69 is connected to the CCD sensor 61 and the initializing signal circuit 82.

Figure 5:
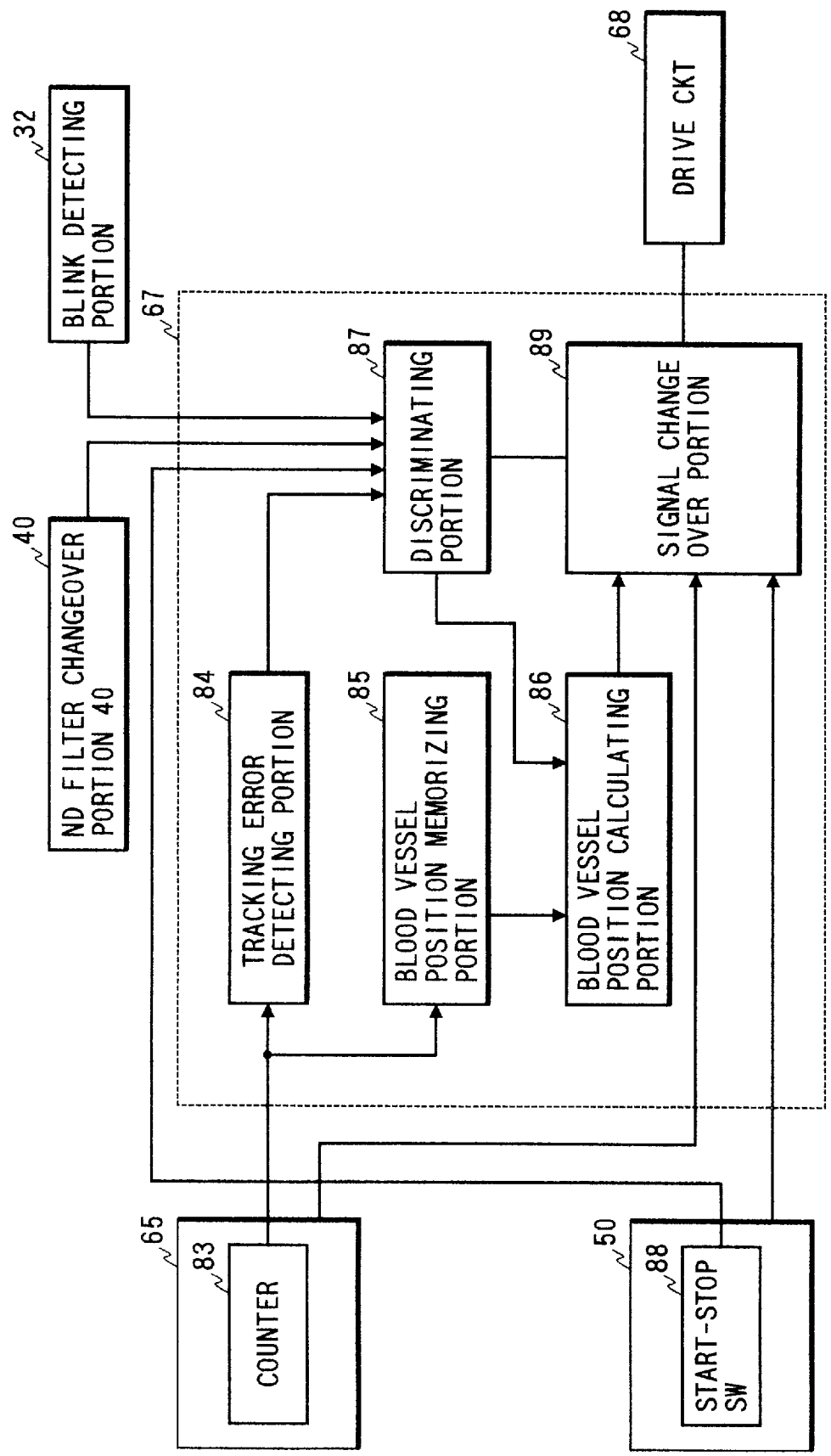
FIG. 5 is a block circuit diagram showing the operation of a control device when automatic tracking is resumed.

FIG. 5 shows a block diagram of the control device 67, and also shows a mechanism for automatically resuming blood flow measurement when tracking operation is poor. The control device 67 is adapted to judge the tracking state and send out a drive signal to the galvanometric mirrors 46 and 49 suitable for that state through the drive circuit 68.

The output of a counter 83 in the tracking control means 65 is connected to a tracking error detecting portion 84 for detecting the tracking impossible state and a blood vessel position memorizing portion 85, the output of which is connected to a blood vessel position calculating portion 86. The output of the tracking error detecting portion 84, the changeover state signal of the ND filter changeover portion 40 and the output of the blink detecting unit 32 are connected to the discriminating portion 87 of the control device 67, and the output of the start-stop switch 88 of the operating rod 50 is also connected thereto. Also, the output of the discriminating portion 87 is connected to a signal changeover portion 89 and the blood vessel position calculating portion 86. Three kinds of signals, i.e., the output of the blood vessel position calculating portion 86, the output of the operating rod 50 and the output of the tracking control means 65 having a tracking mechanism, are connected to the signal changeover portion 89, the output of which is connected to the drive circuit 68.

In the eye fundus blood flow meter having the above-described construction, the illuminating light emitted from the illuminating light source 21 is imaged on the ring slip 27 through the band-pass filter 23, the condenser lens 24, the mirror 25 and the field lens 26. The illuminating light having emerged from the ring slit 27 is once imaged on the apertured mirror 30 by the relay lenses 28 and 29, whereafter it passes through the image rotator 31 and is imaged on the pupil of the eye E to be examined by the objective lens 22, and substantially uniformly illuminates the fundus Ea of the eye E to be examined.

The reflected light from the fundus Ea of the eye again passes through the objective lens 22 and the image rotator 31, and enters the image stabilizer 35 via the central aperture of the apertured mirror 30 and the aperture 34. At this time, the operating rod 50 is operated to thereby rotatively move the galvanometric mirrors 46 and 49 and designate a region to be measured on the fundus Ea of the eye.

The light beam having emerged from the image stabilizer 35 enters the observation optical system 36 and is distributed to two optical paths by the half mirror 53 via the focusing lens 51 and the dichroic mirror 52, and one of the two light beams is imaged on the television camera 55 via the lens 54, and an eye fundus image Ea' is displayed on the monochromatic television monitor 56, and an examiner effects the alignment of the apparatus and the selection of the region to be measured while observing the eye fundus image Ea'.

Figure 6:
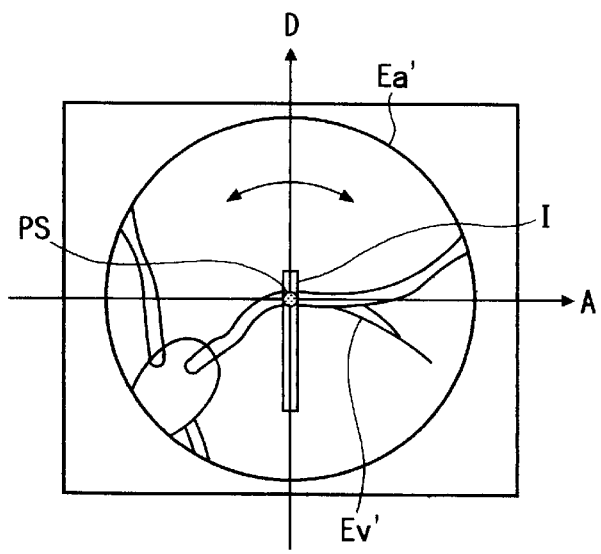
FIG. 6 is an illustration of an observed eye fundus image.

Referring to FIG. 6, which shows the eye fundus image Ea' observed on the television monitor 56, the direction of the coordinate axis A represents the direction of the line of intersection between a plane passing through the centers of the pair of small mirrors 33a and 33b and fundus Ea of the eye, and the image PS of the laser beam for measurement is a spot image representing the region to be measured. The examiner first operates the operating rod 50 and makes the spot image PS coincident with the blood vessel Ev to be measured. At this time, the spot image PS is fixed while remaining positioned at the center relative to the examiner's field of view, and the eye fundus image Ea' moves and is observed.

When the image rotator 31 is rotated thereafter, the eye fundus image Ea' rotates about the center of the field of view in the direction of arrow, and the examiner makes the direction of the blood flow in the blood vessel Ev to be measured coincident with the direction of the axis A. This means that $\beta=0°$ is brought about in FIG. 1B. When the region to be measured is selected in this manner, a one-dimensional image in the direction of an axis D, orthogonal to the axis A, is picked up by the CCD sensor 61 of the blood vessel detecting system 57, and the galvanometric mirror 46 of the image stabilizer 35 is driven so that the position of the blood vessel Ev in the direction of the axis D, may become constant during measurement.

Also, the other light beam distributed by the half mirror 53 enters the blood vessel detecting system 57 and is imaged on the one-dimensional CCD sensor 61 via the mirror 58, the lens 59 and the filter 60. At this time, the filter 60 intercepts the wavelength of the laser beam of the light source 41 for measurement and therefore, this laser beam does not arrive at the CCD sensor 61, which thus picks up a blood vessel image by only the illuminating light from the illuminating light source 21. The CCD sensor 61 of the blood vessel detecting system 57 forms an image enlarged more than the image on the television camera 55, and a detailed blood vessel image is displayed on the display unit 63 via the blood vessel diameter calculating unit 66. The output of the CCD sensor 61 is also sent to the tracking control means 65, which thus produces a tracking signal for the drive circuit 68.

Figure 7:
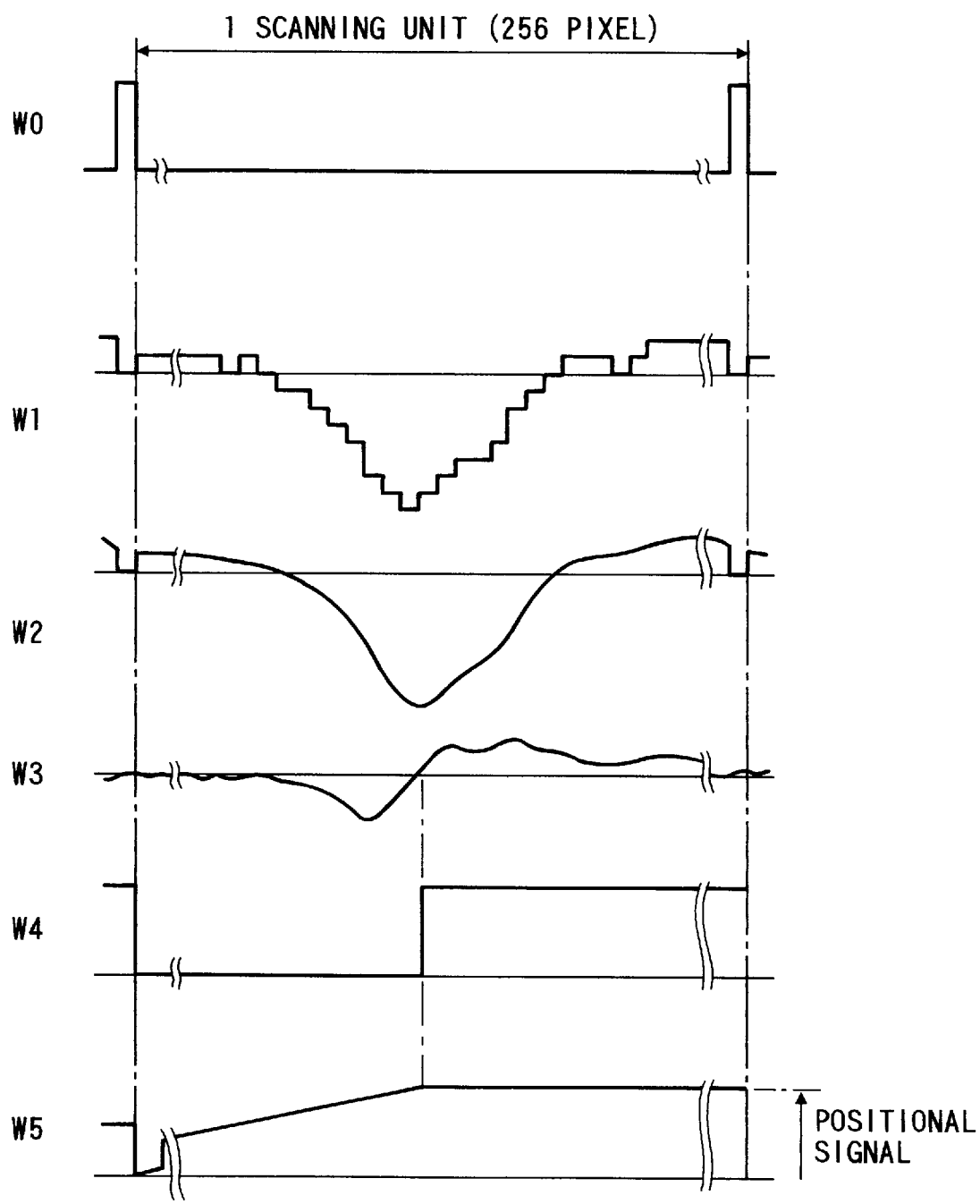
FIG. 7 is a timing chart of a blood vessel position calculation.

Referring to FIG. 7, which shows a timing chart of the operation of producing a tracking signal for the drive circuit 68 by the tracking control means 65, the image output W1 of the one-dimensional CCD 61 comprising 256 pixels is amplified by the amplifier 70 of the tracking control means 65 shown in FIGS. 2A and 2B, whereafter it is shaped into a waveform W2 by the suitable low-pass filter 71 which does not deform the waveform of the actual eye fundus image Ea' and is differentiated by the differentiator 72 and becomes a differentiated waveform W3. Thereafter, it passes through the zero-cross comparator 73 and is binarized and becomes a waveform W4. The count value the waveform W4 counts between low levels is cleared during each measurement in synchronism with the signal SS from the synchronizing signal generating circuit 69, and the count value at the end of one scan corresponds to the blood vessel position as indicated by a waveform W5. A position signal for driving the galvanometric mirrors 46 and 49 is outputted to the drive circuit 68 so that this count value may become a predetermined value. In the present embodiment, this operation is performed at a rate of 1 kHz, whereby control is automatically effected so as to keep the relation among the position of the blood vessel, which is the object to be measured moved by the movement of the eyeball, the applied position of the laser beam, and the position of the detecting portion constant.

That is, the galvanometric mirror 46 makes a movement which automatically compensates for the fine fixation movement of the eye E to be examined by the operation of the drive circuit 68, and once the examiner designates the blood vessel position to be measured, the blood vessel at this position is image-picked up on the CCD sensor 61, and at this time, the laser beam for measurement is made coaxial with the observation optical system 36 by the half mirror 53, and thereafter returns reversely along the optical path and is directed onto the fundus Ea of the eye, and is projected always onto the designated blood vessel to be measured.

The laser beam for measurement forms a spot on the aperture 38 at a position conjugate with the fundus Ea of the eye by the lens 37 before it is coupled to the observation optical system 36 by the dichroic mirror 52, and the conjugate relation thereof is adjusted via the lens 37. Accordingly, when the examiner moves the focusing lens 51 on the optical axis to thereby effect the focusing of the fundus Ea of the eye, the image pickup surface of the television camera 55 and the image pickup surface of the one-dimensional CCD sensor 61 become conjugate with the fundus Ea of the eye at the same time. Of the measurement laser beam reflected from the blood vessel Ev on the fundus Ea of the eye, the light beam rectilinearly travelling through the apertured mirror 30 is intactly directed to the observation optical system 36 and acts as an index indicative of the region to be measured on the television camera 55.

Figure 8:
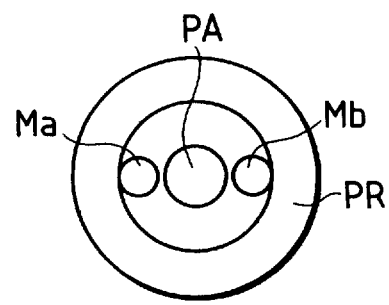
FIG. 8 is an illustration of an irradiating light beam and an observation light beam.

On the other hand, a part of the measurement laser beam is reflected by the pair of small mirrors 33a and 33b provided rearwardly of the apertured mirror 30. FIG. 8 represents the disposition of each light beam on the pupil, the images Ma and Mb by the pair of small mirrors 33a and 33b represent the position of the light beam to be received, the image PA of the aperture 34 represents the position of the light beam for observation and the laser beam for measurement, and the image PR of the light projecting portion of the ring slit 27 represents the position of the illuminating light beam. The angle facing the region to be measured from the images Ma and Mb corresponds to the measurement angle α in FIG. 1A.

According to the principle of the velocity detection described with respect to the example of the conventional art, the blood flow velocity is obtained from the interference signal between the scattered reflected light from the blood vessel wall and the scattered reflected light in the blood flow and therefore, even if the fundus Ea of the eye moves in the direction of the axis A during measurement, the result of measurement will not be affected if the blood vessel Ev is made parallel to the axis A. On the other hand, when the fundus Ea of the eye has moved in the direction of the axis D orthogonal to the axis A, the laser beam for measurement deviates from the blood vessel Ev and measurement becomes impossible. Accordingly, the blood vessel detecting system 57 and the image stabilizer 35 cooperate with each other to effect one-dimensional tracking in the direction of this axis D.

The light beams reflected by the pair of small mirrors 33a and 33b are condensed by the lenses 42a and 42b, are received by the photomultipliers 43a and 43b and are photoelectrically converted and become electrical signals, which are sent to the spectrum analyzers 77a and 77b of FIG. 3 in synchronism with the synchronizing signal SS from the synchronizing signal generating circuit 69. These signals are Fourier-transformed and are inputted to the signal processing means 78, in which two maximum blood flow quantities fmax1 and fmax2 are calculated and the blood flow velocity is found. This blood flow velocity data is sent to the blood flow quantity calculating unit 63 and the display unit 64.

Figure 9:
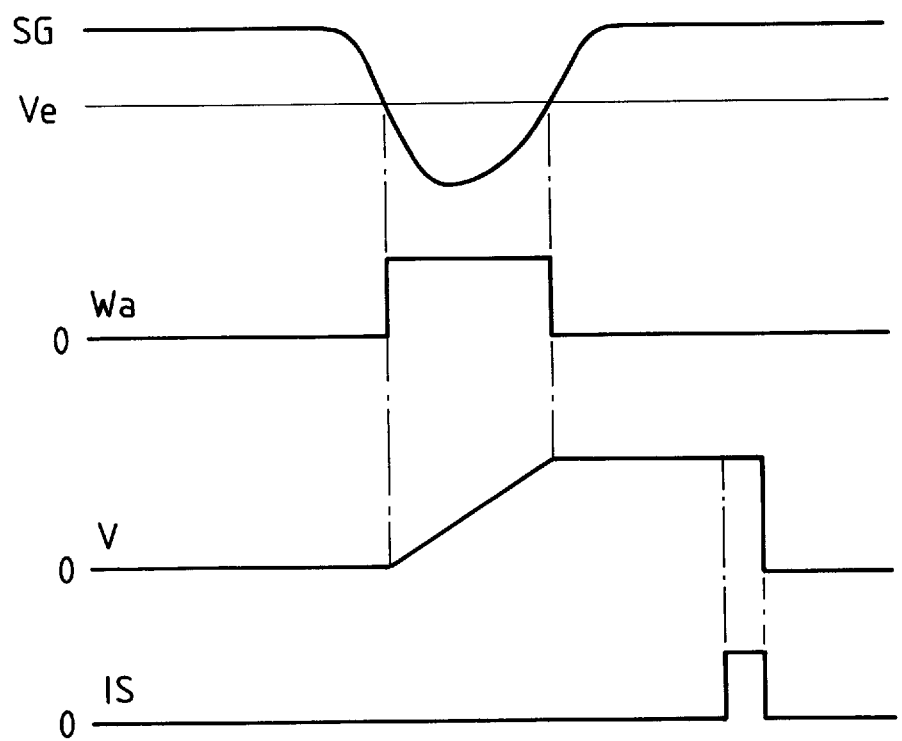
FIG. 9 is a timing chart of the blood vessel diameter calculating unit.

FIG. 9 shows a timing chart of the blood vessel diameter calculation, and in the blood vessel diameter calculating unit 66, a signal SG from the CCD sensor 61 is inputted to the comparator 79 in synchronism with the synchronizing signal SS from the synchronizing signal generating circuit 69. The comparator 79 compares a predetermined reference voltage Ve from the reference voltage generating circuit 80 and the signal SG with each other, and finds an output Wa exceeding the reference voltage Ve, and integrates the output and obtains potential V. This potential V is cleared by a signal IS from the initializing signal circuit 82 during each measurement, and the output potential V of the integrator 81 immediately before the potential V is cleared corresponds to the blood vessel diameter d.

The thus found blood vessel diameter d, like the blood flow velocity, is sent to the blood flow quantity calculating unit 63 and the display unit 64, and in the blood flow quantity calculating unit 63, the blood flow quantity is calculated from the blood flow velocity and the blood vessel diameter supplied from the blood flow velocity calculating unit 62 and the blood vessel diameter calculating unit 66, respectively. The blood flow velocity, the blood vessel diameter and the blood flow quantity can be used, for example, for the diagnosis of arteriosclerosis, diabetes, etc.

In the present embodiment, the synchronizing signal SS from the synchronizing signal generating circuit 69 is used to progress the operation of the circuit, but the synchronizing signal generating circuit 69 may be replaced by a clock circuit to progress the operation by a clock signal. That is, the clock signal from the clock circuit can be supplied to the blood vessel diameter calculating unit 66 and the blood flow velocity calculating unit 62, and the clock signal can be counted by a unique internal counter, and the internal counter can be set so as to determine the calculation timing.

In the mechanism for automatically resuming the blood flow measurement when the tracking operation is bad which is shown in FIG. 5, the tracking error detecting portion 84 manages the count value outputted from the tracking control means 65, and when a numerical value outside the range of management is detected, it outputs an error signal. Also, the ND filter changeover portion 40 outputs data indicating the occurrence of a tracking impossible state occurring due to the interception of the laser beam when it changes over the ND filter for adjusting the quantity of light of the laser, and the blink detecting portion 32 outputs data indicating the occurrence of a tracking impossible state in which the optical path is intercepted by the eyelid. Besides these, a decrease in the quantity of scattered light from the fundus of the eye, the impossibility of the calculation of the blood flow velocity, etc., may be inputted to the discriminating portion 87 to thereby effect the control of tracking. The discriminating portion 87 judges the states of these signals and send instructions, and the signal changeover portion 89 changes over the output on the basis of the instructions.

Figure 10:
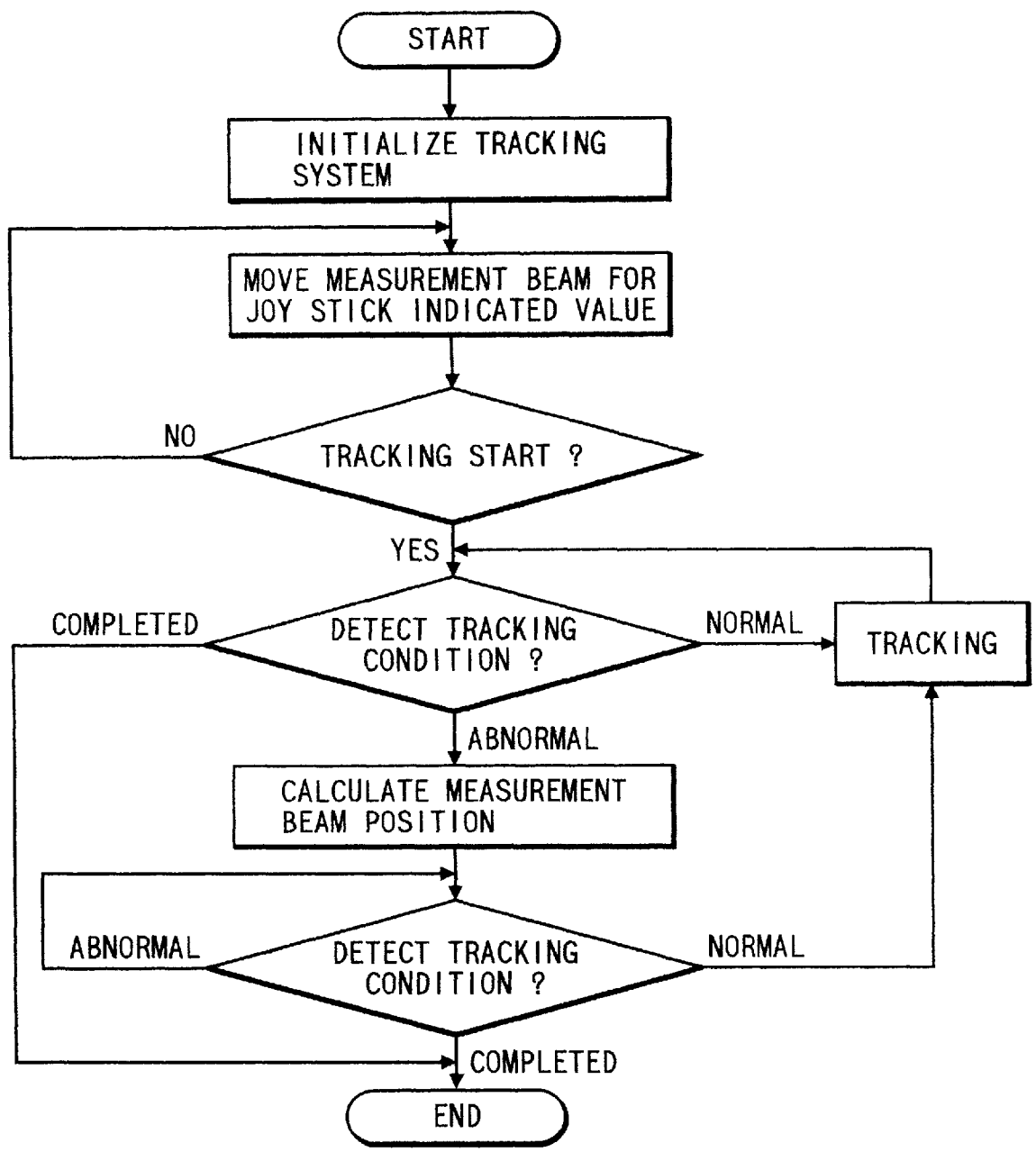
FIG. 10 is a flow chart of the operation of the control device when automatic tracking is resumed.

Referring to FIG. 10, which shows a flow chart of the operation of automatically resuming blood flow measurement, the control device 67 effects initialization so that the measurement beam spot may be applied to the center of the observation field of view at the start of the application of the measurement beam before tracking is entered, and outputs an operation signal to the drive circuit 68 in accordance with the instructions of the operating rod 50 to thereby move the measurement beam to a position indicated by the examiner.

Next, when a measurement starting signal is outputted from the start-stop switch 88 of the operating rod 50, the discriminating portion 87 confirms an error signal from the tracking error detecting portion 84, the ND filter changeover portion 40 and the blink detecting portion 32. When it confirms that the error signal is not being outputted from these, the discriminating portion 87 outputs to the signal changeover means 89 a signal which makes the input from the tracking control means 65 effective, and the signal changeover means 89 outputs a signal from the tracking control means 65 to the drive circuit 68 to thereby effect eye fundus tracking.

When a tracking error arises during the tracking operation, the error signal from the tracking error detecting portion 84 is inputted to the discriminating portion 87 and therefore, the discriminating portion 87 outputs a calculation starting signal for the restart position to the blood vessel position calculating portion 86 and at the same time, outputs to the signal changeover portion 89 a signal which makes the input from the blood vessel position calculating portion 86 effective. When the calculation starting signal for the restart position is inputted, the blood vessel position calculating portion 86 calculates the restart position to the drive circuit 68. The signal changeover portion 89 outputs the signal from the blood vessel position calculating portion 86 to the drive circuit 68 and therefore, the drive circuit 68 sets the galvanometric mirror 46 at the restart position, and tracking is interrupted. When the tracking error becomes null again, the input of the error signal to the discriminating portion 87 becomes null and therefore, the discriminating portion 87 outputs a calculation terminating signal for the restart position to the blood vessel position calculating portion 86 and at the same time, outputs a signal which makes the input from the tracking control means 65 effective.

When by the above-described operation, a tracking error is caused during eye fundus tracking, the tracking is temporarily interrupted and the apparatus waits at the restart position, and when the tracking error becomes null, the tracking can be resumed from the restart position. Also, when it is desired to discontinue measurement, the start-stop switch 88 of the operating rod 50 is operated, whereby a stop signal is detected and tracking can be discontinued. Further, eye fundus tracking can be resumed by a similar operation in a tracking impossible state occurring due to the laser beam being intercepted when the ND filter is changed over, or in a tracking impossible state in which the optical path is intercepted by the eyelid.

Next, the measurement beam application position at the restart is calculated in the blood vessel position calculating portion 86. 50 numbers of blood vessel position data relative to the present measuring apparatus converted from the counter 83 of the tracking control means 65 are stored at an interval of 10 msec. in the blood vessel position memorizing portion 85, and the eye fundus blood vessel position at the restart of tracking is foreseen on the basis of these stored positions.

The impossibility of tracking when the count value outputted from the tracking control portion 84 is a value outside the range or when the ND filter for adjusting the quantity of light of the laser is changed over is not a tracking error occurring due to the movement of the eyeball and therefore, the position immediately before the tracking error occurs is designed to be outputted. In the case of a tracking impossible state in which the optical path is intercepted by the eyelid during blinking, the blink results in the movement of the eyeball and therefore, if the position immediately before the tracking error has occurred is outputted, the blood vessel cannot be detected at the restart of tracking and therefore, in such case, the restart position is calculated on the basis of the stored blood vessel position data.

Since a blink usually ends in 100 msec., the position before 100 msec. is defined as the restart position, but depending on an examinee's will, there is conceivable a case where the examinee closes his eyes for 100 msec. or longer and therefore, in such case, the probability with which tracking can be resumed with the center position of the amplitude of the relative position data resulting from the movement of the eyeball as the restart position is highest, and the average value of 50 numbers of data is defined as the restart position.

Besides this, there are also conceivable a system for carrying out a weighted mean process, a system in which those of blood vessel position data which are low in frequency are thinned to reduce the influences of the abnormality of the output of the counter 83, the abnormality of the fixating state, the malfunction due to the deficiency of the quantity of light from the fundus Ea of the eye caused at the early stage of the examinee's blink, etc., and a system in which in order to attach importance to new data, the new data is multiplied by such a coefficient that the weight becomes greater in proportion to time to thereby find the mean.

To detect a blink by the blink detecting portion 32, for example, a light beam may be projected onto the eye E to be examined, and the reflected light from the eyelid, iris and pupil of the eye E to be examined may be continuously detected, and the eyelid covers may be detected from the received shape of this reflected light. Also, there may be provided a form in which a portion which becomes a dark portion on the fundus Ea of the eye is intentionally provided in the measurement beam application optical path to thereby pick up the eye fundus image including the dark portion, and a blink can be detected by detecting the contrast thereof. Such an example will be shown below.

Figure 1A:
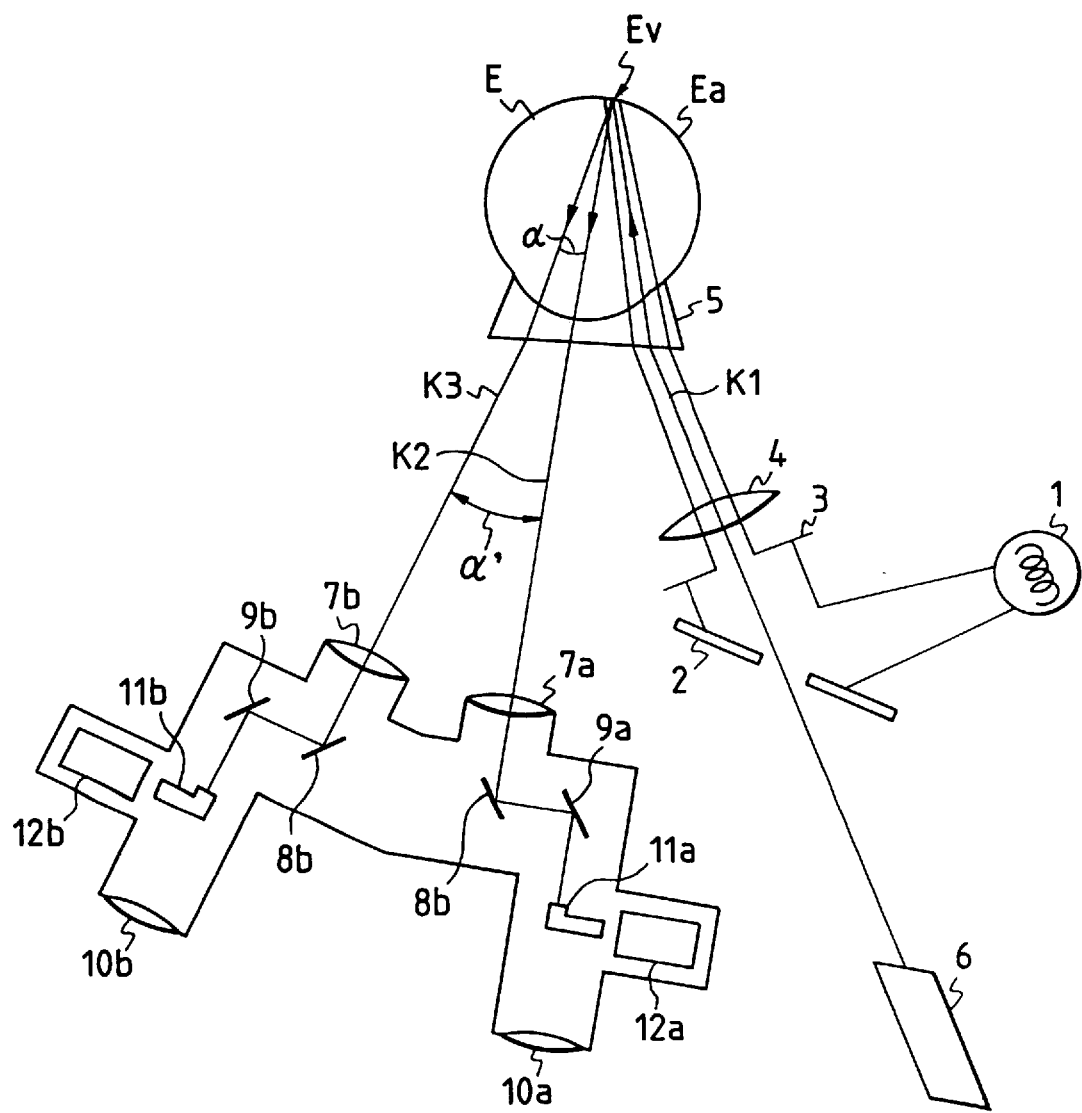
FIG. 1A shows the construction of an example of the conventional art.
Figure 1B:
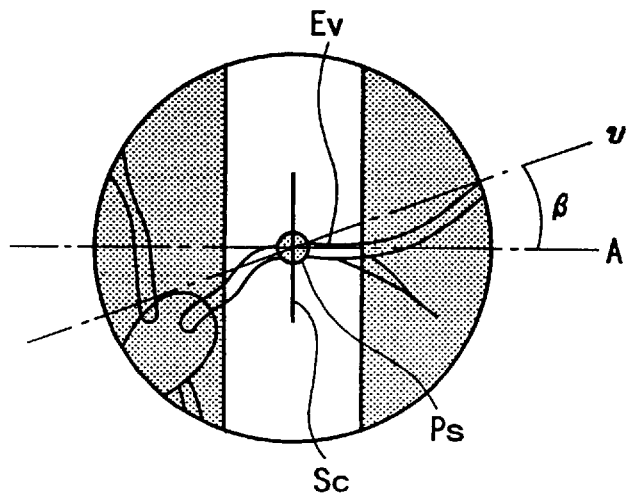
FIG. 1B is an illustration of an observation image.
Figure 1C:
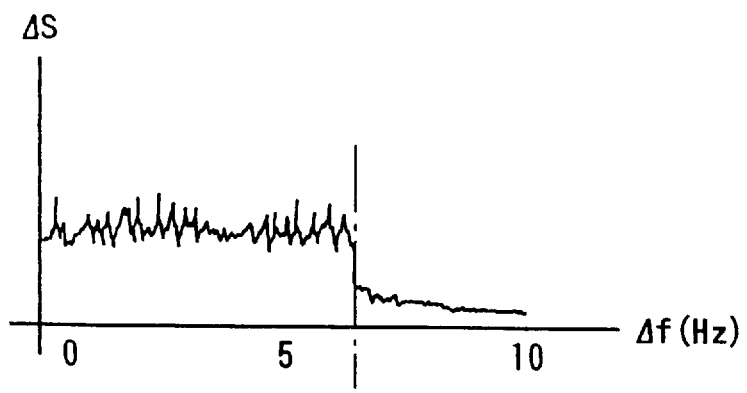
FIG. 1C is a graph of a frequency analysis of a light reception signal.
Figure 11:
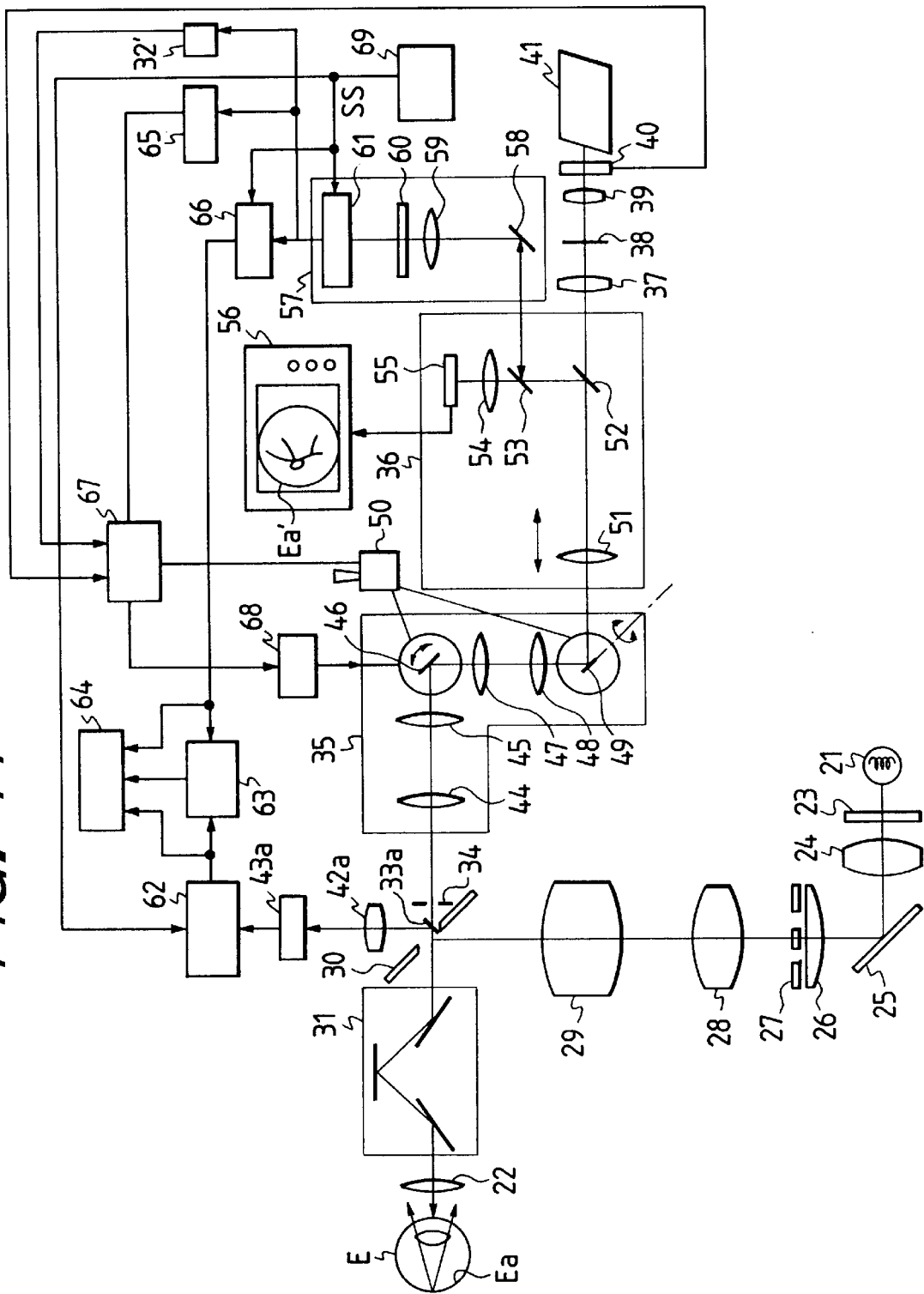
FIG. 11 shows the construction of a second embodiment of the present invention.
Figure 12:
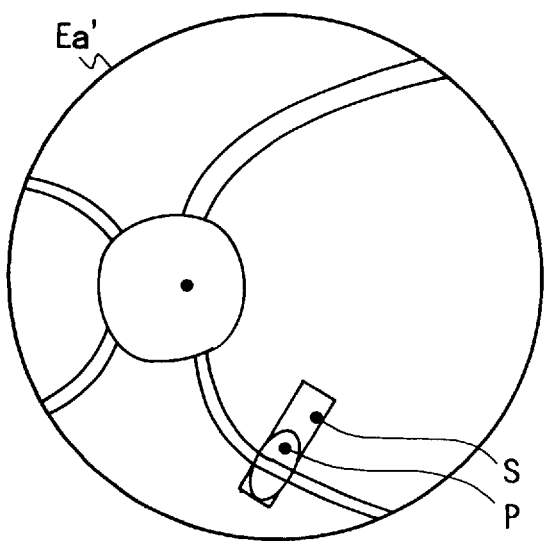
FIG. 12 is an illustration of the image picked-up area of an eye fundus image.
Figure 13:
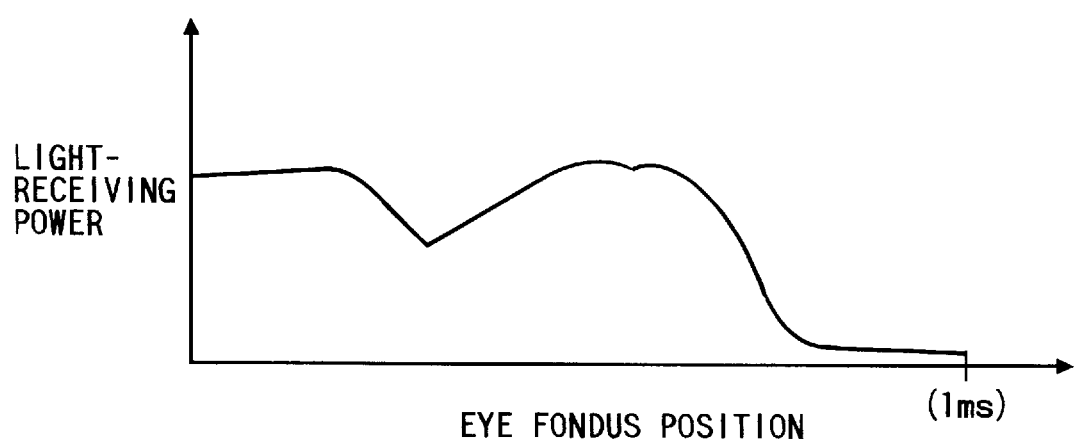
FIG. 13 is a graph of the output of a CCD.

FIG. 11 shows the construction of a second embodiment of the present invention, and in FIG. 11, the same reference numerals as those in FIGS. 1A, 1B and 1C designate the same members. A blink detecting portion 32 is not provided in front of the eye E to be examined, and the output of a one-dimensional CCD 61 is connected to a blink detecting portion 32' comprised of a circuit, and as shown in FIG. 12, an image pickup area S in a range wider than the application area P of a measurement beam is image-picked up by the CCD 61. Here, the application optical path of the measurement beam and a photographing optical path are the same optical path and therefore, even if tracking is effected, the relation between the measurement beam and the image pickup device always becomes constant, and the output signal of the CCD 61 becomes such as shown in FIG. 13.

Accordingly, by comparing the contrast of the measurement beam application area P and the area to which the measurement beam is not applied, it becomes possible to detect a blink. When the contrast is great, it means that the eye is a state in which the eye fundus image Ea' is caught, and when the contrast becomes small, it indicates the occurrence of a state in which a measurement beam spot P is not applied to the fundus Ea of the eye, such as a state in which a blink is being performed, and when the contrast assumes a predetermined value or greater thereafter, the blink is regarded as having ended and a tracking possible signal is generated, and on the basis of this signal, the control device 67 restarts tracking.

Referring to FIG. 14, which shows a flow chart of the automatic tracking resuming operation by blink detection, the blink detecting portion 32' detects a blink during eye fundus tracking, and the blood vessel position calculating portion 86 foresees and calculates the examinee's eye fundus blood vessel position at the restart of tracking on the basis of the stored blood vessel position. On the basis of this calculated value, the position of the measurement beam is determined and the angles of the galvanometric mirrors 46 and 49 are controlled, whereafter when the completion of the blink is detected, eye fundus tracking is automatically resumed.

While the above embodiments have been described with respect to an eye fundus blood flow meter, the tracking apparatus of the present invention may be provided even in the case of another ophthalmologic photographing apparatus or measuring apparatus having a tracking mechanism for eyeball movement other than this meter, whereby when a tracking impossible state occurs due to a malfunction such as a blink state, tracking can be discontinued, and after the malfunction has been eliminated, tracking can be automatically resumed to thereby continue photographing and measurement.

What is claimed is:

1. An apparatus for observing a fundus of an eye to be examined comprising:

a tracking mechanism for tracking a portion of the fundus of the eye to be examined;

detecting means, disposed independently from said tracking mechanism, for detecting a blink of the eye to be examined; and controlling means for controlling said tracking mechanism according to an output of said detecting means.

2. An apparatus according to claim 1, wherein said controlling means controls said tracking mechanism to stop tracking a portion of the eye fundus when a blink is detected by said detecting means.

3. An apparatus according to claim 2, wherein said controlling means controls said tracking mechanism to restart tracking from the state where tracking is stopped, when the blink is detected to be completed by said detecting means.

4. An apparatus according to claim 3, wherein said controlling means stores a plurality of tracking states of said tracking mechanism before the blink is generated and controls said tracking mechanism to restart tracking at the time of completion of the blink, based on the stored tracking states.

5. An apparatus according to claim 1, wherein the portion to be tracked is a blood vessel of a fundus of the eye to be examined.

6. An apparatus according to claim 5, further comprising a blood flow state detecting system for detecting a state of blood flow flowing through the blood vessel, said blood flow state detecting system comprising:

a beam illuminating unit for illuminating the portion of the fundus of eye to be examined with a measuring beam; and a light receiving unit for receiving reflected light of the measuring beam reflected by the portion to measure the state of the blood flow.

7. An apparatus according to claim 6, wherein said tracking mechanism comprises:

a tracking beam illuminating unit for illuminating a portion of the fundus of the eye to be examined with a tracking beam for tracking;

a tracking beam receiving unit for receiving a tracking beam reflected by the portion, and a controlling unit for controlling a position to be illuminated by the measuring beam according to the receiving state of said tracking beam receiving unit.

* * * * *